United States Patent
Kalla et al.

(10) Patent No.: US 8,094,879 B2
(45) Date of Patent: Jan. 10, 2012

(54) METHODS FOR RECOMMENDING PERSONAL CARE PRODUCT AND TOOLS THEREFOR

(75) Inventors: Karen Kalla, Cincinnati, OH (US); Patricia Alison LaFleur, Shewsbury, PA (US); Joseph Miller, Cincinnati, OH (US); Grover Owens, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 12/949,250

(22) Filed: Nov. 18, 2010

(65) Prior Publication Data

US 2011/0064307 A1    Mar. 17, 2011

Related U.S. Application Data (63) Continuation of application No. 11/780,817, filed on Jul. 20, 2007, now Pat. No. 7,856,118.

(51) Int. Cl.
*G06K 9/00* (2006.01)
*G09B 25/00* (2006.01)

(52) U.S. Cl. ........ 382/100; 382/118; 382/128; 382/181; 382/217; 600/306; 434/377

(58) Field of Classification Search .......... 382/100, 382/118, 128, 181, 217–220; 715/810–839; 600/306; 434/377
See application file for complete search history.

(56) References Cited

U.S. PATENT DOCUMENTS

| | | | | |
|---|---|---|---|---|
| 1,741,080 A | * | 12/1929 | Stenz | 434/100 |
| 1,960,669 A | | 5/1934 | Freedman | |
| 4,232,334 A | * | 11/1980 | Dyson | 348/77 |
| 4,555,179 A | | 11/1985 | Langerholc et al. | |
| 3,278,099 A | | 3/1988 | Kinney | |
| 4,842,523 A | * | 6/1989 | Bourdier et al. | 434/371 |
| 5,178,169 A | * | 1/1993 | Lamle | 132/319 |
| 5,313,267 A | * | 5/1994 | MacFarlane et al. | 356/405 |
| 5,562,109 A | * | 10/1996 | Tobiason | 132/200 |
| 5,836,872 A | | 11/1998 | Kenet | |
| 5,852,675 A | * | 12/1998 | Matsuo et al. | 382/167 |
| 5,865,196 A | | 2/1999 | Foote | |
| 6,000,407 A | * | 12/1999 | Galazin | 132/200 |

(Continued)

FOREIGN PATENT DOCUMENTS

DE    3137326    3/1983

(Continued)

OTHER PUBLICATIONS

PCT International Search Report, date mailed: Jan. 23, 2009, 6 pages.

*Primary Examiner* — Manav Seth
(74) *Attorney, Agent, or Firm* — John G. Powell (57) ABSTRACT

A tool including a frame that includes an aperture and a boundary marker disposed about the aperture. The boundary marker includes a first marker region disposed about the aperture and a second marker region disposed about the first marker region. The color of the first marker region is different from the color of the second marker region. The tool also includes a color correction scale disposed proximate to the aperture. The color correction scale has at least a first color correction region and a second color correction region. The color of the first and second color correction regions each have an LCh value of between L=73.5 C=15.3 h=55.6 and L=32.5 C=11.6 h=48.3.

18 Claims, 6 Drawing Sheets

U.S. PATENT DOCUMENTS

| | | | |
|---|---|---|---|
| 6,178,341 B1 * | 1/2001 | Macfarlane et al. | 600/310 |
| 6,271,920 B1 | 8/2001 | Macfarlane | |
| 6,421,125 B1 * | 7/2002 | Tarumoto | 356/421 |
| 6,724,480 B2 * | 4/2004 | de Rigal et al. | 356/422 |
| 6,807,297 B1 * | 10/2004 | Tankovich et al. | 382/162 |
| 6,809,809 B2 | 10/2004 | Kinney | |
| 6,832,913 B2 * | 12/2004 | Lehmann | 433/26 |
| 6,856,861 B2 * | 2/2005 | Dirksing et al. | 700/239 |
| 6,886,964 B2 | 5/2005 | Gardiner | |
| 6,941,011 B2 | 9/2005 | Roylance | |
| 6,941,028 B2 | 9/2005 | Kimmel | |
| 6,985,230 B2 * | 1/2006 | De Rigal et al. | 356/421 |
| 6,985,622 B2 | 1/2006 | Hubel | |
| 7,064,830 B2 | 6/2006 | Giorgianni | |
| 7,118,374 B2 * | 10/2006 | Culp | 433/26 |
| 7,193,712 B2 | 3/2007 | Sottery | |
| 7,274,453 B2 | 9/2007 | Sottery | |
| 7,317,818 B2 | 1/2008 | Lefebvre | |
| 7,359,529 B2 | 4/2008 | Lee | |
| 7,499,076 B2 * | 3/2009 | Goto | 348/77 |
| 7,522,768 B2 * | 4/2009 | Bhatti et al. | 382/167 |
| 7,634,538 B2 * | 12/2009 | Mori et al. | 709/204 |
| 2002/0010556 A1 | 1/2002 | Marapane | |
| 2002/0065456 A1 * | 5/2002 | Bazin et al. | 600/407 |
| 2003/0063300 A1 | 4/2003 | Rubinstenn | |
| 2004/0122299 A1 | 6/2004 | Nakata | |
| 2004/0125996 A1 * | 7/2004 | Eddowes et al. | 382/128 |
| 2004/0264750 A1 * | 12/2004 | Znaiden et al. | 382/128 |
| 2005/0025728 A1 | 2/2005 | De Rigal | |
| 2006/0007424 A1 | 1/2006 | Hubner | |
| 2006/0036135 A1 | 2/2006 | Kern | |
| 2006/0085274 A1 | 4/2006 | Sottery | |
| 2006/0129411 A1 | 6/2006 | Bhatti | |
| 2007/0058858 A1 * | 3/2007 | Harville et al. | 382/165 |
| 2007/0058859 A1 | 3/2007 | Baker | |
| 2007/0058860 A1 | 3/2007 | Harville | |
| 2007/0071314 A1 | 3/2007 | Bhatti | |
| 2007/0110305 A1 | 5/2007 | Barcovschi | |
| 2007/0118820 A1 | 5/2007 | Hatakeyama | |
| 2007/0175788 A1 | 8/2007 | Holba | |
| 2007/0217690 A1 | 9/2007 | Dempski | |
| 2008/0059218 A1 | 3/2008 | Sottery | |
| 2008/0260218 A1 | 10/2008 | Smith | |

FOREIGN PATENT DOCUMENTS

| | | |
|---|---|---|
| EP | 1471462 | 10/2004 |
| EP | 1471463 | 10/2004 |
| EP | 1484907 | 8/2006 |
| JP | 2002189918 | 7/2002 |
| JP | 2002203238 | 7/2002 |
| JP | 2003149051 | 5/2003 |
| JP | 2005148797 | 6/2005 |
| JP | 2006024203 | 1/2006 |
| WO | WO 03003300 | 1/2003 |
| WO | WO2006044562 | 4/2006 |

* cited by examiner

METHODS FOR RECOMMENDING PERSONAL CARE PRODUCT AND TOOLS THEREFOR

CROSS REFERENCE TO RELATED APPLICATION

This application is a continuation of application Ser. No. 11/780.817, filed Jul. 20, 2007, now U.S. Pat. No. 7,856,118, which is incorporated herein by reference.

TECHNICAL FIELD

The present disclosure relates in general to recommendation systems and, in particular, to methods and systems for personal care product recommendations.

BACKGROUND

Countless individuals all over the world seek to improve their physical appearance through the use of personal care products, such as cosmetics and skin care treatments. Recognizing the market for such products, manufacturers have provided an extremely large range of products from which consumers may choose. It thus comes as no surprise that the individual consumer finds it difficult to determine what type of products to apply.

One of the issues central to the selection of many personal care products is color. In this regard, it is not only the color of the product that may be important, but the color or tone of the individual's skin as well and how well the color of the product matches the color or tone of the skin. The individual's perception of the color of the product and of his or her own skin may be influenced by factors such as the lighting available at the time the selection is made, which may be different than the lighting existing under conditions of normal use. The individual may attempt to compensate for the varying conditions by attempting to imagine how a product might look when applied in use, but this may make an already subjective process even more prone to inconsistency.

One way in which retailers attempt to assist the individual consumer is by having beauty consultants available at their cosmetics counters. These consultants are then charged with assisting customers in identifying personal care products aimed at improving the customer's appearance. Because of their training and/or experience, they may be able to provide a more consistent result than if the individual was to attempt to make his or her selections unassisted.

However, such consultations remain subjective. The same customer going to two different consultants may receive two different recommendations. Consultation results can vary from visit to visit, even with the same counselor and client. In addition, employment of beauty consultants increases the cost of the personal care products, and many customers do not want to be inconvenienced by approaching a beauty consultant.

SUMMARY OF THE INVENTION

In order to provide a solution to the problems described above, a tool comprising a frame comprising an aperture and a boundary marker disposed about the aperture is disclosed herein. The boundary marker comprises a first marker region disposed about the aperture and a second marker region disposed about the first marker region. The color of the first marker region is different from the color of the second marker region. The tool also comprises a color correction scale disposed proximate to the aperture. The color correction scale has at least a first color correction region and a second color correction region. The color of the first and second color correction regions each have an LCh value of between L=73.5 C=15.3 h=55.6 and L=32.5 C=11.6 h=48.3.

BRIEF DESCRIPTION OF THE DRAWINGS

While the specification concludes with claims particularly pointing out and distinctly claiming the subject matter that is regarded as the present invention, it is believed that the invention will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

DETAILED DESCRIPTION

The following description includes reference to different colors and color spaces. In that regard, the following conventions may be followed. These terms may be defined with additional language in the remaining portions of the specification.

"Black" refers to a color having a luminance value of less than about 40 and a chroma value of less than about 60, more specifically L of less that about 30 and C of less than about 30, even more specifically L of less than about 20 and C of less than about 30, and still more specifically L of less than about 20 and C of less than about 15, wherein the illuminant is D65 with a 10-degree observer.

"Chroma value" ("$C^{ab}*$" or "C") refers to the vector distance from the center of the color space to the measured color; it is intended to designate saturation or intensity of a color and distinguishes color intensity from clarity (i.e. vividness vs.

dullness). The lower the chroma of the color, i.e. the less its intensity, the closer the color is to being a grey color.

"Hue value" ("$h^{ab}$" or "h") refers to the basic colors, such as red, yellow or blue. Hue is defined in a plane with red, yellow, green, and blue being 90 degrees apart from one another. A color's hue is an angle in that plane.

"Lightness value" ("L*" or "L") refers to the perception of light to dark of the color. Black has low lightness (theoretically approaching 0) and white has high lightness.

"LCh color space" is a color measurement convention wherein the L value, C value and h value may be plotted in a three dimensional space using polar components where L is an axis, h is an angle, and C is the distance away from the L axis along the h angle, as defined in the CIE L*$C^{ab}$*$h^{ab}$ color space system "Light" color and "dark" color, or "the lightest" color and "the darkest" color (and any permutations thereof) are relative terms meant to refer to that in the present context of color cosmetics, one ("light" or "lighter") color is perceived by an ordinary observer as lighter than the other ("dark" or "darker") color. Typically, but not necessarily, a "light" or "lighter" color may have the Luminance value "L" that is greater than that of the "dark" or "darker" color. Other color characteristics, such as, for example, Chroma value "C" and/or hue, may affect the consumers' perception as to what can be considered a "light" or "lighter" color relative to a "dark" or "darker" color.

"Target substrate" is a portion of a consumer's body, including, without limitation, skin, hair, lips, nails, eyes, and teeth, to which portion sample areas of the color-selection tool of the present invention can be compared for the purpose of choosing the correct cosmetic color.

In general, the methods, systems and apparatuses described herein use an electromagnetic capture device in a system for recommending a personal care product. It is intended that the user, for example a retail customer, be able to operate the apparatus according to the present disclosure without assistance, although it is not limited as such. Specifically, the user self-aligns the substrate to be measured, e.g., a portion of his/her body, which may be a non-homogeneous/homogeneous shiny or matte substrate. One or more calibration standards may also be aligned with the apparatus, and the user triggers an electromagnetic measurement. In response, the apparatus captures electromagnetic waves from the substrate. Digital data is determined from the captured electromagnetic waves. Based on the digital data, the customer is given certain choices and/or informed of certain recommendations, e.g., personal care product recommendations.

According to one embodiment, the apparatus used with the standards also includes an electromagnetic source and a plurality of filters in a predetermined arrangement to be used in measuring an electromagnetic radiation response property associated with a substrate, In this embodiment, at least a portion of the waves generated by the source are captured after the waves pass through a first polarized filter, reflect from the user, and pass through a second polarized filter arranged in a cross polar arrangement with respect to the first polarized filter, Additionally, this apparatus may capture electromagnetic waves that pass through an attenuating filter and reflect from the one or more calibration standards. In such a circumstance, the digital data obtained may be used to calibrate and/or recalibrate the apparatus. Additional information regarding this embodiment may be found in copending U.S. application Ser. No. 10/965,534.

Figure 1:
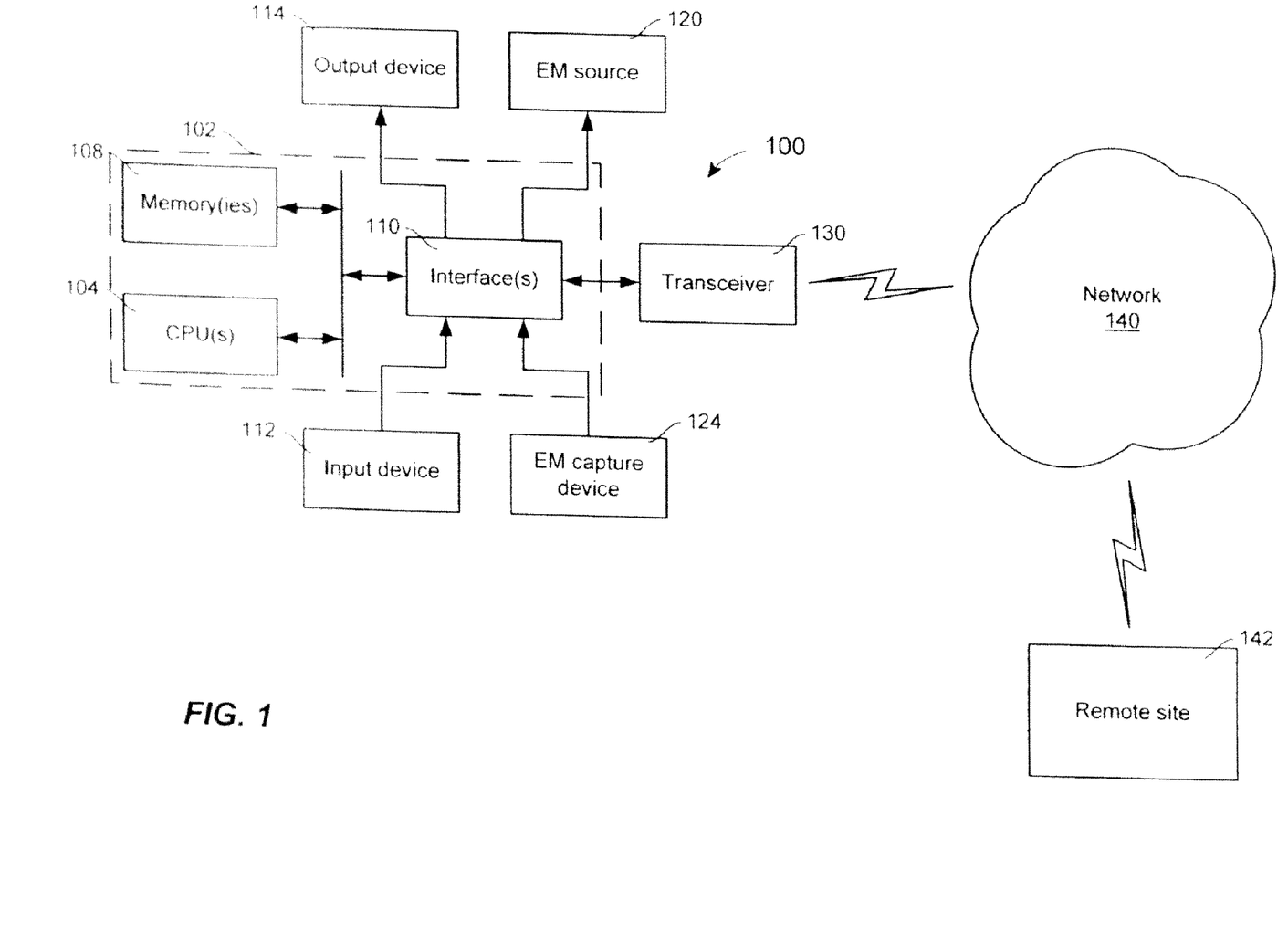
FIG. 1 is a block diagram of an apparatus for use with methods and systems for recommending personal care products according to the present disclosure.

A block diagram of an apparatus 100 structured to create and capture electromagnetic waves according to another embodiment is illustrated in FIG. 1, which apparatus may be used in conjunction with a remote site for the generation of personal care product recommendations. The apparatus 100 includes a controller 102 which may include one or more processing units 104 operatively coupled to one or more memory devices 108 and one or more interface circuits 110. In turn, the one or more interface circuits 110 may be operatively coupled to one or more input devices 112, one or more output devices 114, an electromagnetic source 120 and an electromagnetic capture device 124.

The one or more processing units 104 may be of a variety of types, for example including microprocessors, microcontrollers, digital signal processors, specialized mathematical processors, etc. The memory device(s) 108 may include volatile memory and/or non-volatile memory, and may be in the form of internal and/or external memory (e.g., flash cards, memory) sticks, etc.). The memory device(s) 108 may store one or more programs that control the function of the apparatus. The memory device(s) 108 may also store data indicative of screen displays, bit maps, user instructions, personal identification information, demographic data, digitized images, color data, light intensity data, histogram data, and/or other data used by the apparatus 100 and/or collected by the apparatus 100. The interface circuit 110 may implement any of a variety of standards, such as Ethernet, Universal Serial Bus (USB), and/or one or more proprietary standards.

The one or more input devices 112 may be used to receive data, signals, identification information, commands, and/or other information from the user of the apparatus 100. For example, the one or more input device 112 may include one or more keys or buttons, a voice or gesture recognition system and/or a touch screen. The one or more output devices 114 may be used to display or convey prompts, instructions, data, recommendations and/or other information to the user of the apparatus 100. For example, the one or more output devices 114 may include one or more displays, lights, and/or speakers. Where the apparatus is in the form of a user-operated mobile device or system, as described below, the output devices 114 may include a liquid crystal display (LCD) and a speaker.

The capture device 124 generates color data from a substrate of interest and one or more calibration standards, potentially in conjunction with the source 120, such as a xenon flash lamp, a linear flash, a ring flash or other light sources, The capture devices 124 may include charge coupled devices (CCDs), complementary metal oxide semiconductor (CMOS) devices, junction field effect transistor (JFETs) devices, linear photo diode arrays or other photo-electronic sensing devices. As also noted above, the substrate of interest may take any of a number of forms, including for example the skin, eyes or teeth of the user of the apparatus 100.

The calibration standard(s) may include a sample with one or more regions whose light intensity characteristics are known to the system. In fact, a tool may be designed which assists in the capture process and the calibration process. FIGS. 2-5 illustrate several such tools.

Figure 2:
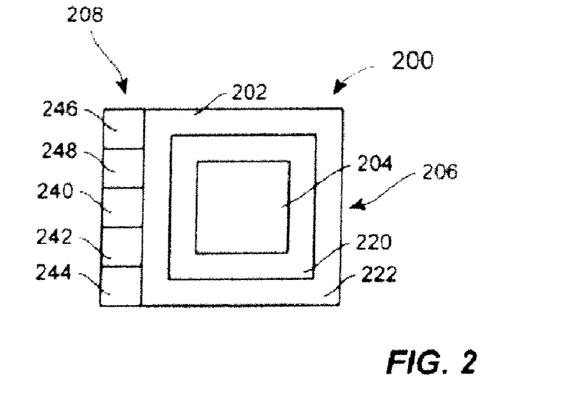
FIG. 2 is a schematic of a tool for use with the apparatus and system of FIG. 1.

FIG. 2 illustrates a tool 200. The tool 200 includes a frame 202 with an aperture 204, a boundary marker 206, and a color correction scale 208, and in certain embodiments the aperture 204, the boundary marker 206 and the color correction scale 208 are coplanar. It will be recognized that the tool 200 need not include all of these elements according to certain embodiments, and the elements need not be coplanar. However, as illustrated, the tool 200 of FIG. 2 includes all three structures and they are coplanar.

Turning first to the frame 202, it will be recognized that the frame 202 may be made of a material such that the tool 200 may be intended to be reusable or disposable. For example, the frame 202 may be made of a plastic material where the intent is to permit the user to use the tool 200 multiple times. Alternatively, the frame 202 may be made of a paper material where the intent is to permit the user to dispose of the tool 200 after use. Of course, the material used will not necessarily dictate whether a tool 200 will be reusable or disposable, for plastic tools may well be recycled after a single use, and a paper tool may still be useful after a single or a limited number of uses. However, it will be recognized that where a large number of the tools are available at a point of purchase, it may be preferable to have the tool disposable for hygienic reasons.

Turning next to the aperture 204, the aperture 204 is formed to display at least a portion of a substrate of interest in the aperture 204, which may be a substance such as skin, nails or hair. The number of apertures included may vary between tools 200. Also, the shape of the apertures may vary between tools 200.

For instance, while FIG. 2 illustrates a tool 200 with a single aperture 204, other tools may have multiple apertures to display different substrates or portions of the same substrate. Where multiple apertures are used to display different substrates of interest, for instance skin and nails or skin and teeth, the multiple apertures may separate the substrates of interest to facilitate the imaging process. Alternatively, where multiple apertures are used to display different portions of the same substrate of interest, this may be done to provide separate samples for comparison purposes.

Figure 4:
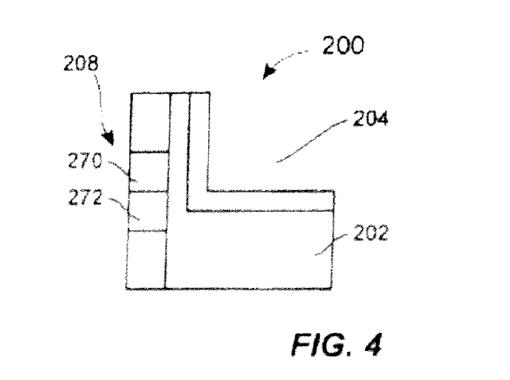
FIG. 4 is a schematic of another alternative tool.

It will be recognized that the shape of the aperture 204 illustrated in FIG. 2 has a closed perimeter. According to other embodiments, such as that illustrated in FIG. 4, the aperture may have an open perimeter, with no structure limiting the extent of the aperture along one or more sides. As illustrated in FIG. 4, the perimeter is open on two sides. Thus, it is not necessary that the aperture be in the form of a hole or slot, bounded on all sides (e.g., a notch or a side).

Figure 5:
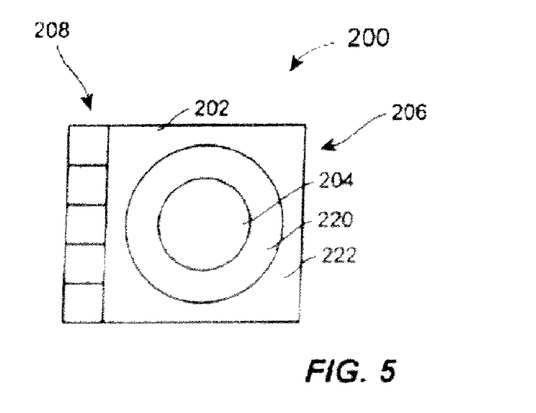
FIG. 5 is a schematic of a still further alternative tool.

It will also be recognized that the shape of the aperture 204 illustrated in FIG. 2 is square. It is not necessary for the aperture to have a square shape. A circular shape is illustrated in FIG. 5, and another shape, bounded by an L-shaped frame 202, is illustrated in FIG. 4. While shapes that have roughly comparable measurements in two-dimensions may facilitate image process, shapes that are more narrow than they are tall, and thus more one-dimensional in nature, may also be used. For that matter, as alluded to previously, the aperture may be defined by a single side of the frame.

Regardless of the shape of the aperture 204, a boundary marker 206 may be disposed about the aperture 204. Again, there is considerable diversity in the shape and composition of the boundary marker 206. Moreover, while the boundary marker 206 may be used to indicate at least a portion of the boundary of the aperture 204, the marker may have other uses as well, depending on the structure of the marker 206. For instance, the marker 206 may also be used in determining one or more corrective factors to be used to modify an image taken using the tool for background illumination, as is explained below. In fact, different corrective factors may be applied in different directions.

As illustrated in FIG. 2, the boundary marker 206 may include at least two different marker regions, a first marker region 220 and a second marker region 222, although other embodiments may include a single marker region. The first marker region 220 is disposed about the aperture 204. Because the aperture 204 has a closed perimeter, the first marker region 220 appears to have a ring shape. The second marker region 222 is then disposed about the first marker region. As illustrated, the second marker region 222 has a ring shape, like the first marker region 220, and is concentric with the first marker region 220. According to other embodiments, a third marker region 224 may also be included, as in FIG. 3.

Figure 3:
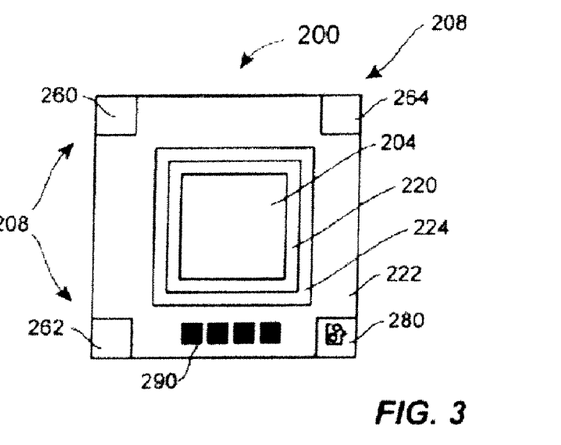
FIG. 3 is a schematic of an alternative tool.

In the foregoing paragraph, it is not intended for "about" to be limited to referencing only those embodiments wherein the marker region entirely surrounds the aperture 204, as illustrated in FIGS. 2 and 3, Instead, "about" is intended to indicate that the marker region lies along side of the aperture 204, irrespective of the closed or open nature of the aperture 204. Additionally, "about" is used to describe those situations where the marker 206 is not continuous, for the marker 206 may be discontinuous (e.g., dashes).

According to the present disclosure, the colors of the first marker region 220 and the second marker region 222 may be different. For, that matter, where a third marker region 224 is included, as in FIG. 3, this marker region may have a color that is different than the colors of the first marker region 220 and the second marker region 222.

According to a first embodiment, the colors of the first marker region 220 and the second marker region 222 may be optimized for determination of the region-of-interest (ROI) of any image taken using the tool 200. This may be done by having the first marker region 220 be black and the second marker region 222 be white. Alternatively, the first marker region 220 may have a color that is optimized for imaging in one channel of a color space, while the second marker region 222 may have a color that is optimized for imaging in another channel of the color space. For example, the first marker region 220 may have a G value that is at least one order of magnitude larger than its R value, while the second marker region 222 may have an R value that is at least one order of magnitude larger than its G value. According to other embodiments, the R and G values may differ by at least two orders of magnitude.

An advantage of using colors other than black and white for the marker regions 220, 222 is that it may not be necessary to include a third marker region 224 so as to use the boundary marker 206 to correct for background illumination. Where black and white are used for the marker regions 220, 222, the colors may cause the portion of the image associated with the boundary marker 206 be of limited use in determining a gradient from which to determine a background correction. By contrast, where colors other than black or white are used, it may be possible to develop one or more such gradients. In fact, multiple gradients may be used in the horizontal and vertical directions. Even where black and white are used, the introduction of a third marker region 224 of grey may permit a gradient to be determined for the boundary marker 206.

The tool 200 also includes a color correction scale 208. FIGS. 2-5 illustrate different embodiments of color correction scales, wherein the number of regions of the color correction scale and the placement of the scale and/or its constituent regions varies. It will be recognized that aspects of each of the embodiments may be interchanged with aspects of the other embodiments to provide additional embodiments that, while not illustrated, remain within the scope of the present disclosure Because the color correction scale may include a series of regions, each region representing a skin tone, the color correction scale may also be referred to as a skin tone scale, even though the scale may include regions other than those representing skin tones.

As illustrated in FIG. 2, the color correction scale 208 includes a first color correction region 240, a second color correction region 242, and a third color correction region 244, each of the color correction regions 240, 242, 244 being a different skin tone. That is, the color of the first region 240 is different than the color of the second region 242, and the color of the third region 244 is different than the colors of the first and second regions 240, 242.

According to certain embodiments, the LCh values of color corrective regions representative of skin tones may vary between about L=73.5, C=15.3, h=55.6 and about L=32.5, C=11.6, h=48.3 wherein the illuminant is D65 with a 10-degree observer. Within this range, different populations may have different mean skin tones. For example, a first population may have a mean skin tone of about L=66.0, C=21.4, h=52.3, while a second population may have a mean skin tone of about L=48.8, C=23.1, h=57.3, and a third population may have a mean skin tone of about L=63.3, C=22.8, h=56.6.

It will be recognized that a diverse set of different color correction scales using skin tones may be configured within the range recited above. For example, one exemplary skin tone scale may include the limits of the range and at least one population mean skin tone. According to another embodiment, the skin tone scale may include the limits of the range and at least two population mean skin tones. For that matter, a skin tone scale may be constructed to include a mean skin tone value for a population and at least one other, preferably at least two other, skin tones representative of that population. For example, where a population has a mean skin tone of about L=48.8, C=23.1, h=57.3, two other regions may be included, one with a skin tone of about L=564, C=253, h=60.4 and another with a skin tone of about L=41.3. C=20.2, h=54.1. As another example, where a population has a mean skin tone of about L=63.3, C=22.8, h=56.6, two other regions may be included, one with a skin tone of about L=66.7. C=20.8, h=56.0 and another with a skin tone of about L=59.9, C=24.3, h=55.5. Other possible combinations are possible to cover a desired range.

The matching between the colors of the skin tones represented in the regions 240, 242, 244 may be judged according to a variety of different standards, any of which may provide an operable system. However, colors judged to be a match for a skin tone under a less-stringent standard provide different results in use than colors judged to be a match for an actual skin tone under a more-stringent standard, For instance, a color used for one of the regions 240, 242, 244 may be said to be a match of an actual skin tone at a single lighting condition, for example wherein the illuminant is D65 with a 10-degree observer. Alternatively, a color may be said to be a match at two or more lighting conditions, for example a first wherein the illuminant is D65 with a either a 2-degree or a 10-degree observer and a second wherein the illuminant is A, F2, F7, F11, TL84 with either a 2-degree or 10-degree observer. Potential measurement devices include, but should not be limited to, an Ocean Optics' USB4000 fiber optic spectrophotometer or a Datacolor Microflash integrating sphere spectrophotometer. Further, instead of using D65, another daylight source standard may be used, such as D50 or D55. As a very stringent standard, a color may be said to match an actual skin tone if a full spectral match occurs over the reflectance spectra of skin, from 400-700 nanometers (nm). It will be recognized that these standards should be thought of as a non-limiting set of examples, and others will be known to those skilled in the art.

Further, the color correction scale 208 illustrated in FIG. 2 comprises a fourth color correction region 246 and a fifth color correction region 248. According to one embodiment, the fourth color correction region 246 may be black, while the fifth color correction 248 region may be white. According to another embodiment, the fourth and fifth color correction regions may be different shades of grey, a light grey and a dark grey, for example.

As illustrated, the regions 240, 242, 244 of the scale 208 are arranged such that the second region 242 abuts the first region 240 and the third region 244 abuts the second region 242. Similarly, the fourth region 246 abuts the fifth region 248, while the fifth region 248 abuts the first region 240. It will be recognized that the scale 208 also abuts the boundary marker 206.

However, it is not necessary that the regions 240, 242, 244 abut each other or that three color correction regions be included, as illustrated in FIG. 2. While there may be advantages to having the regions 240, 242, 244 abutting each other, it is believed that the regions may be spaced apart and still be useful in the tool 200. As illustrated in FIG. 3, for example, the regions 260, 262, 264 of the scale 208 are disposed about the aperture 204. In particular, the regions 260, 262, 264 are disposed at three of the corners of the square-shaped aperture 204. Further, while the inclusion of three or more regions may enhance the color calibration of an image taken using the tool 200, it may also be possible to use less than three regions as well. As illustrated in FIG. 4, only two regions 270, 272 are included in the scale 208 disposed about the aperture.

Further, while all of the illustrated regions 240-248, 260-264, and 270-272 have a square shape, this is not a requirement of the tool 200 according to the present disclosure. A square shape may have certain advantages over, for example, rectangular shapes, where edge loss in the image taken using the tool might reduce the usefulness of the regions. However, even rectangular shapes may be of sufficient usefulness so as to be used in the tool 200 of the present disclosure. Thus, there is no particular shape for the regions 240-248, 260-264, 270-272 that is required according to the present disclosure.

The regions of the color correction scale 208 may be attached to the frame 202 using a variety of methods. For example, the color correction scale 208 may be fabricated on a separate plate or backing, which plate or backing is then attached to the frame 202. However, it may also be possible to apply or form the color correction scale 208 directly on the frame 202. For example, according to one embodiment, the color correction scale 208 may be applied to the frame using a silk screening method.

According to certain embodiments, the tool 200 may also include instructions disposed on the frame 202. FIG. 3 illustrates one such embodiment, although the instructions may be used with any of the embodiments illustrated. In particular, FIG. 3 includes a region 280 wherein instructions, in pictorial form, are included. In particular, the picture at region 280 illustrates a face with a representation of the tool 200, or at least a portion thereof, disposed on the face. The picture attempts to convey to the user of the tool 200 proper placement of the tool 200 against the target substrate (in this case, the user's face). The picture may also attempt to convey to the user of the tool 200 an approximate proportion of the target substrate to the field of view of the capture device 124. It will be recognized that written instructions may be used in addition to or in substitution for pictorial instructions, such as illustrated in FIG. 3, For example, the pictorial instructions may be provided in the region 280, while written instructions may be disposed on the opposite surface of the frame 202.

Also according to certain embodiments, the tool 200 may include an identifier 290, again with reference to FIG. 3, although the identifier 290 may be used with any of the embodiments illustrated, The identifier may be associated with each individual tool 200, or a single identifier may be used with a plurality of tools 200. For example, a series of different tools 200 may be provided, each with a different color correction scale 208. The different color correction scales 208 may vary between populations, or may be optimized for a particular capture device 124. Each of these tools 200 may have an identifier that is different from other tools 200. The identifier may be simply an alpha-numeric symbol, which symbol is detected from the image or provided by the user of the system using an input device. Alternatively, the identifier may be in the form of a bar code, which bar code is scanned it at the time the image is transmitted or determined from the image when the image is processed. If the bar code is to be determined from the image as processed, the bar code may consist of large blocks, instead of the typical thin lines, to limit the possibility that edge loss will make the identifier unreadable when the image is analyzed.

It will also be recognized that the tool 200 may include a positioning device for the frame and standards, or the combination of frame, standards, filters, lens, etc. Further, the positioning device may include a connector to attach the tool 200 to the target substrate. For example, a strap holder may be used to position the standard against the user's skin, like a wrist-watch band or head band, while the lens and filters may be disposed in an adapter that may be fitted over the capture device 124, although a handle may also be considered a connector as well. Still other alternative positioning devices are illustrated in FIGS. 6-9.

Figure 6:
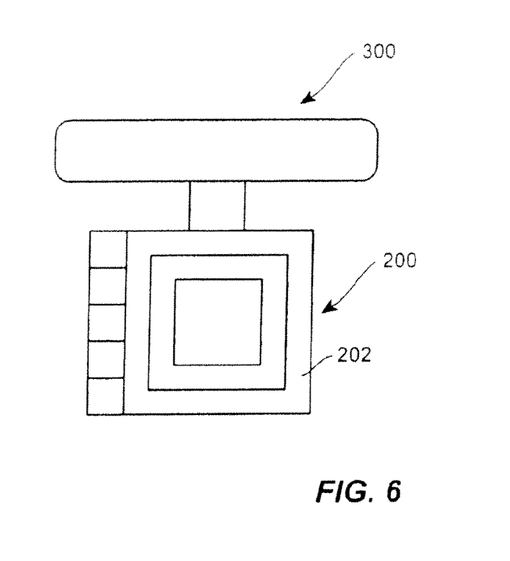
FIG. 6 is a schematic of a positioning device for use with the tools of FIGS. 2-5.
Figure 7:
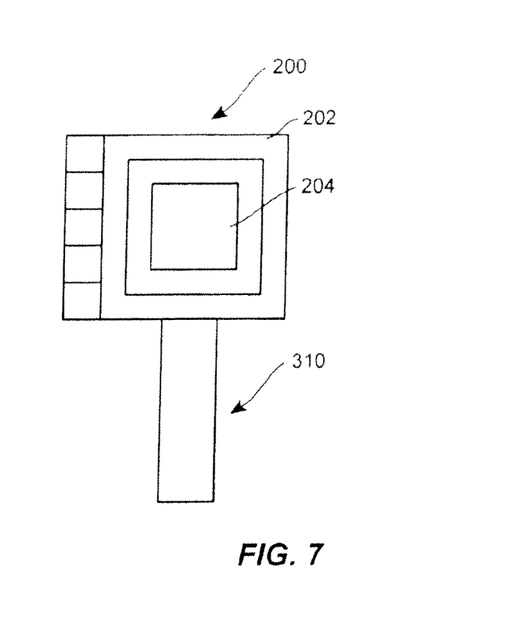
FIG. 7 is a schematic of an alternative positioning device.
Figure 8:
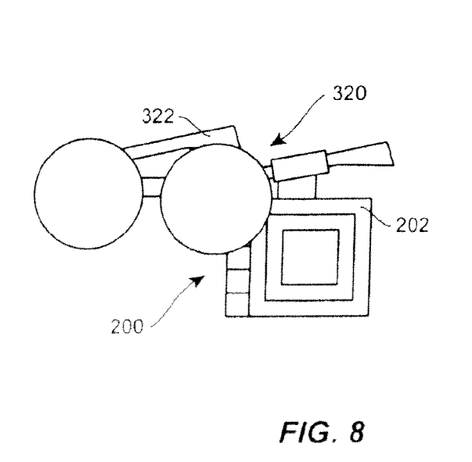
FIG. 8 is a schematic of another alternative positioning device.
Figure 9:
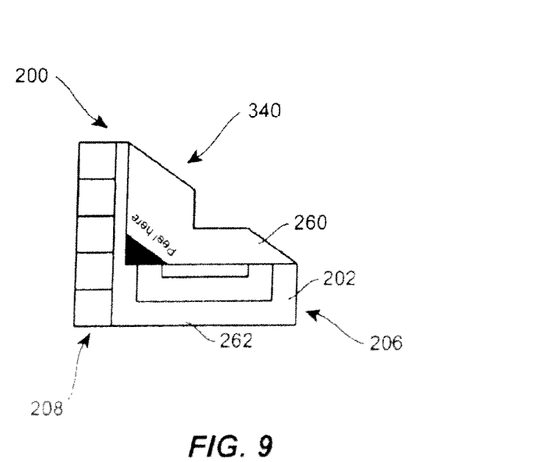
FIG. 9 is a schematic of a still further alternative positioning device, with a corner of the device bent over to expose an opposite surface of the device.

FIG. 6 illustrates an embodiment of the tool 200 wherein the frame 202 is attached to a hat 300 or headband, the hat 300 or headband being positioned on the user's head to properly position the tool. FIG. 7 illustrates an embodiment of the tool 200 wherein the frame 202 is attached to a handle 310, the handle 310 being graspable by the user to connect the frame 202 with the target substrate without the hand of the user being present immediately adjacent the aperture 204. FIG. 8 illustrates an embodiment of the tool 200 wherein the frame 202 of the tool 200 is attached a pair of eyeglasses 320, and in particular the frames 322 of the eyeglasses 320, which positioning device may be useful for maintaining the frame 202 about a target substrate on a cheek of an individual wearing the eyeglasses 320. FIG. 9 illustrates an embodiment of the tool 200 wherein an adhesive strip 340 is attached to the frame 202 of the tool 200 on the surface 260 of the frame 202 opposite the surface 262 on which the boundary marker 206 and the color correction scale 208 are disposed, which positioning device may further free the user's hands to, for example, facilitate the use of the capture device 124 to take the image. According to certain embodiments, the adhesive strip 340 may be in the form of an adhesive strip with a peelable backing, facilitating, storage and ease of use, and preferably uses an adhesive that is releasable when applied to a target substance.

The holder may be omitted altogether. Where the holders are omitted, the standards may be disposed adjacent to or overlying the substrate; for example, where the substrate is skin, the standard(s) may be placed up against the skin of interest and held there manually. In any event, where the standard is held against the skin, tooth, hair or other substrate, it may not be necessary to provide an attenuating filter because the substrate and the standard will be a substantially the same distance relative to the capture device 124.

According then to at least one embodiment of the alternative apparatus 100 illustrated in FIG. 1, the apparatus 100 may be a device or system all or a part of which is mobile, and which may be owned and operated by the user/customer, permitting the user of the apparatus 100 to send for and receive product recommendations at a wide variety of locations. To this end, the apparatus 100 may include a transceiver 130 that permits the apparatus 100 to communicate via a network 140 with a remote site 142 without the use of a wired connection between at least the apparatus 100 and the network 140. The transceiver 130 may be an infrared transceiver, for example. Alternatively, the transceiver may be a radio-frequency (RF) transceiver. Moreover, while the transceiver 130 is illustrated as a single element in FIG. 1, the transceiver 130 may be defined by a combined circuit that provides both transmission and reception, or may be defined by separate circuits for transmission and reception.

Thus, it will be recognized that the apparatus 100 may defined by a mobile unit, such as is commonly referred to as a cellular or mobile telephone, and in particular a cellular or mobile telephone incorporating an digital camera device. Such a device may be referred to herein as a unitary hand-held device. According to such an embodiment, the digital camera may be defined by, at least in part, a CCD, a CMOS, a JFET, or other photo-electronic sensing device. The transceiver 130 may communicate with the network 140 using RF signals in accordance with any of a number of standards.

It will also be recognized that the apparatus 100 may be defined by a mobile system comprised of a combination of separate devices, each device defining a portion of the apparatus 100. For example, the apparatus 100 may include a hand-held device, such as a digital camera, which may include a controller 100, the electromagnetic source 120 and the electromagnetic capture device 124, and a computer, which may also include a controller 100, as well as the input and output devices 112, 114 and the transceiver 130. According to such an embodiment, the digital camera may communicate with the computer over a hard-wire connection (e.g., a cable or the like) or may be in communication with the computer using a wireless connection (e.g., infrared). For that matter, a memory device, such as a compact flash (CF) card or the like, may be removed from the camera and placed in a reader for such devices that is operatively coupled to the computer. It may also be possible for a conventional camera to be used, and the photo provided thereby to be scanned to provide an image that is then transfer to the computer. For its part, the computer may be in communication with the network 140 much like the mobile device above. i.e., using an RE signal in accordance with any of a number of standards. Alternatively, the computer may be in communication with the network 100, for example, by coupling the computer to a router or hub via a wired or wireless (e.g., infrared) link, the router or hub then being in communication with the remainder of the network 140 (e.g., the Internet). For example, the network connection may be, but is not limited to, an Ethernet connection, digital subscriber line (DSL), telephone line, or coaxial cable.

Figure 10:
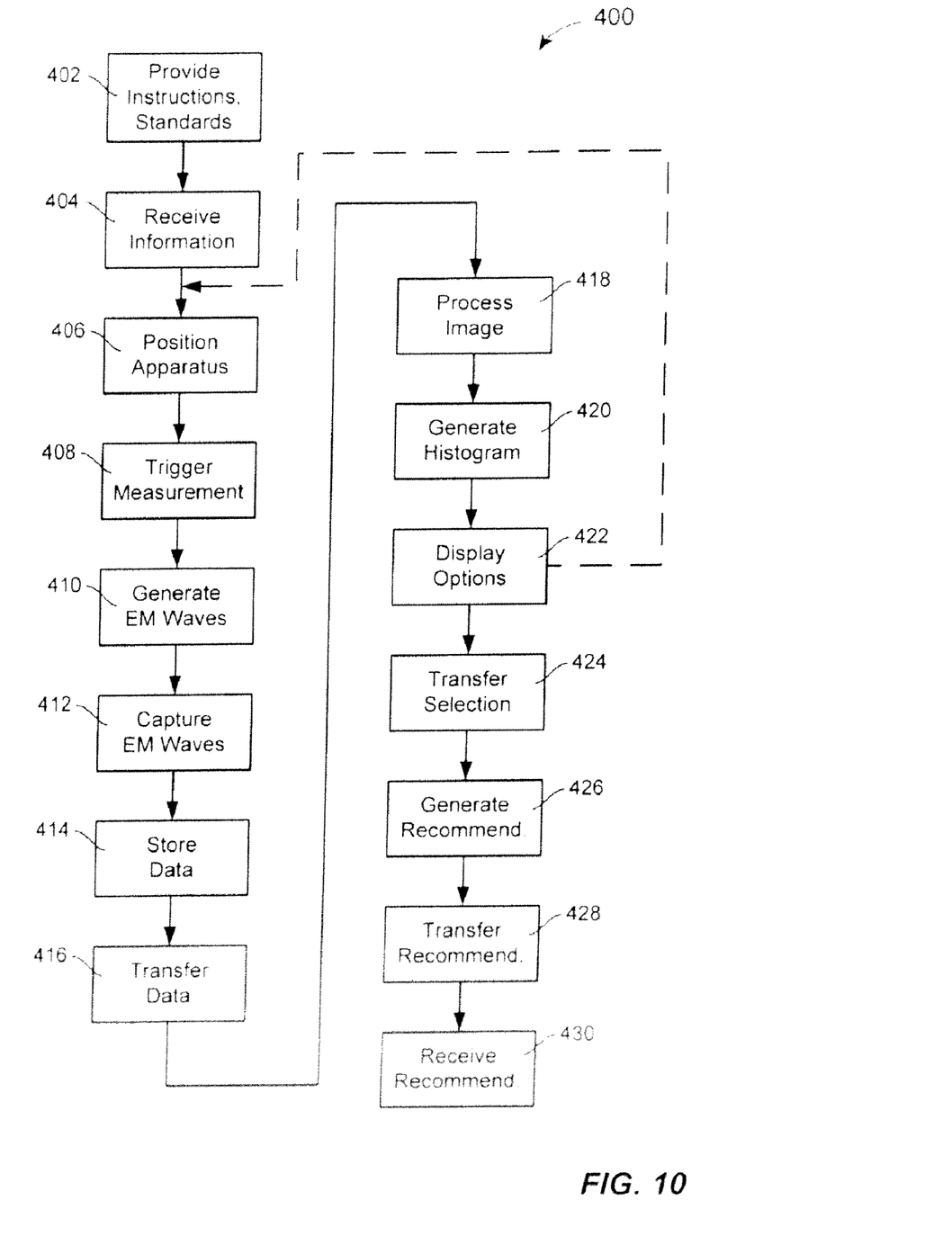
FIG. 10 is a flowchart of a method for measuring an electromagnetic radiation response property associated with a substrate and recommending a personal care product in accordance therewith.

A flowchart of an embodiment of a process 400 for receiving or providing product recommendations is illustrated in FIG. 10, that is, the process includes certain steps that may be performed by the user to request and receive the recommendation, while others may be conducted by a manufacturer, retailer, etc. to generate and provide the recommendation. Although the process 400 is described with reference to the flowchart illustrated in FIG. 10, it will be recognized that many other ways for carrying out the process 400 may exist. For example, the order of the steps may be varied, and steps may be treated as optional or omitted altogether. Also, at least part of the process 400 may be embodied in a software program which is stored in a controller memory 108 and executed by the processing unit 104 in a well known manner. However, certain of the steps of the process 400 may be performed other devices associated with the network 140, the remote site 142 for example.

Generally, the process 400 may begin at blocks 402, 404 depending on the implementation of the apparatus 100. The blocks 402, 404 include activities that provide the user with information and calibration standards, and request information from the user. For example, at the block 402, the user may be provided with the calibration standards and the instructions on the steps that must be carried out to receive the product recommendation, including instructions on how to position the apparatus 100 and the standards, how to trigger the apparatus 100 to obtain a digital representation of the substrate, how to input information on personal preferences, and how to transmit the digital representation and the personal preference information over the network 140. Where the embodiment of the apparatus 100 includes a substrate alignment device, such as a pair of eye positioning frames, the instructions may describe their operation. At the block 404, the user may receive a series of prompts that request certain personal preference and/or personal identification information. In such an instance, the apparatus 100 may receive the personal preference and/or personal identification information via one or more input devices 112 and may store the personal preference and/or personal identification information in a memory 108. This activity may include a form of registration that the user must complete as part of using the system reflected in the method to follow, which registration may also include the selection or assignment of a user identifier and, potentially, a password.

The process 400 continues with the positioning of the electromagnetic source 120, the electromagnetic capture device 124, and standards at block 406. It will be recognized that the exact implementation of this block will vary in accordance with the nature of the embodiment of the apparatus 100, Where the apparatus 100 takes the form of a mobile cell phone with integral digital camera, the block 406 may include the subject or another holding the cell phone so at to point the camera at the substrate of interest. Where the apparatus 100 takes the form of a camera used in combination with a portable computer, the camera may be directed at the substrate, while the location of the computer is not relevant to actions taken at this block. Further, where provided, an alignment device may be used with the substrate. Further, the positioning of the standard(s) may involving laying the standard(s) on the substrate or holding them in place; a holder may be provided to perform this action according to certain embodiments.

Once the user self-aligns the standards and the substrate, for example a portion of his/her body, with the apparatus 100 at block 406, the user triggers an electromagnetic measurement at block 408. In response, the apparatus 100 may generate electromagnetic waves and captures waves from the standard(s) and the substrate at blocks 410, 412, although it will be recognized that the generation of electromagnetic waves is fully optional.

Different waves captured by the electromagnetic capture device 124 at different X-Y coordinates of the electromagnetic capture device 124 may be stored separately in a two-dimensional data matrix at block 114. According to one embodiment of the present disclosure of the apparatus 100, the matrix may be in the form of a digital image, and the representation of the wave captured at a particular X-Y coordinate (pixel) may be a particular light intensity. This two-dimensional matrix may be stored in conjunction with the personal preference and/or the personal identification data associated with this retail customer.

At this point, the information gathered from the user of the apparatus 100 may be transferred from the mobile unit 100 to a remote site 142 via the network 140 at block 416. For example, the identification and personal preference information gathered from the user may be sent to the remote site 142, along with the two-dimensional matrix, via an electronic mail system, with the information either as attachments or embedded in the e-mail. For that matter, the information may be uploaded from the mobile unit/apparatus 100 to the remote site 142 over the network 140, The uploading may occur via the Internet, either via a secure or unsecured site, or may occur via a direct line connection.

The hat intensity values of the matrix may be further processed prior to the veneration or the product recommendation. While these steps may take place within or at the apparatus 100, it may be more convenient to perform these activities at the remote site 142 after the transfer step of block 416. For example, the image may be processed at block 418, and a histogram generated at block 420. For example, the processing at block 418 may include converting the light intensity value from a RGB (red-green-blue) system to a LAB (light-yellow/blue-reel/green) and/or a LCh (light-chroma-hue) system. At the block 420, digital representations of the different waves, or converted versions thereof captured at the different X-Y coordinates of the electromagnetic capture device 124, may be combined into a histogram by determining the light intensity values associated with each of the different X-Y coordinates and counting the number of occurrences of each light intensity value (or each of a range of light intensity values). It will be recognized that it may be converted from the original color space to any other color space at block 418 prior to or after creating a histogram at the block 420.

Figure 11A:
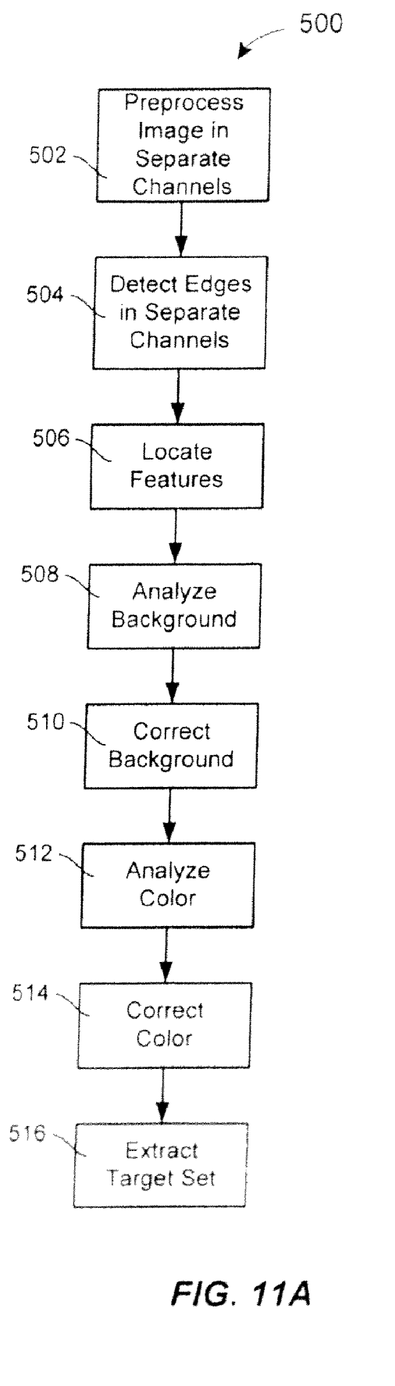
FIG. 11A is a flowchart of a method for processing an image received from the apparatus of FIG. 1.
Figure 11B:
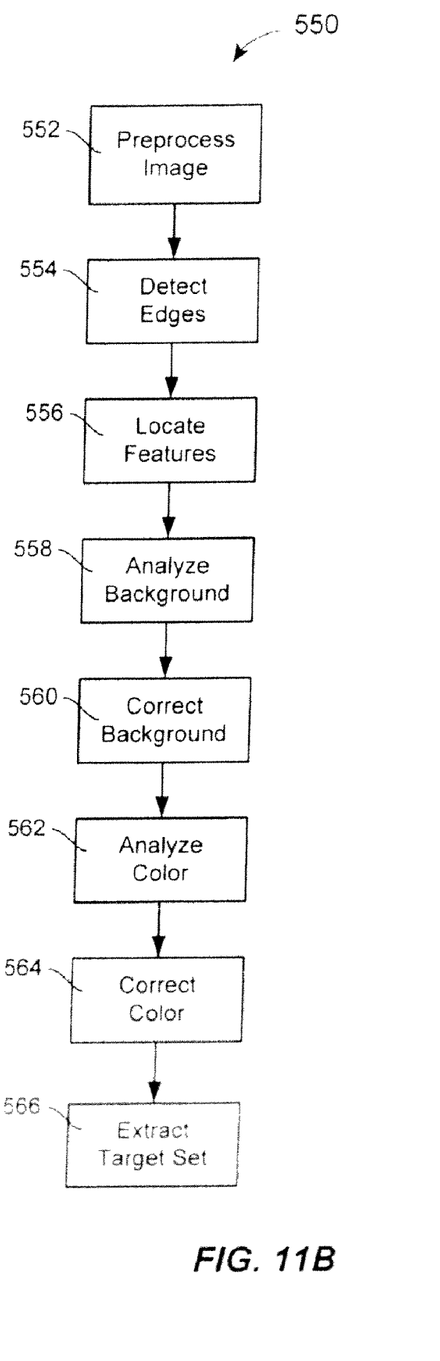
FIG. 11B is a flowchart of an alternative method for processing an image received from the apparatus of FIG. 1.
Figure 11C:
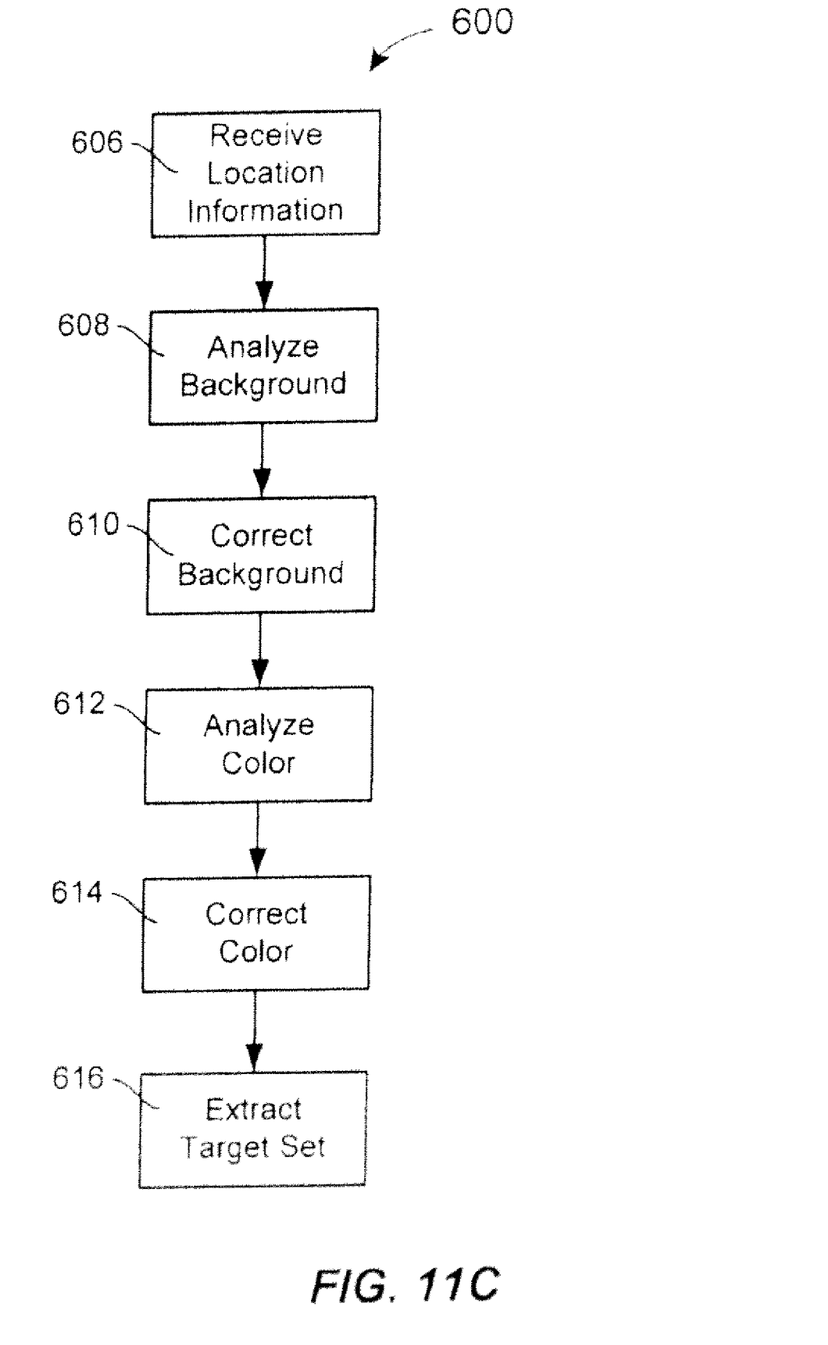
FIG. 11C is a flowchart of another alternative method for processing an image received from the apparatus of FIG. 1.

It will be recognized that additional steps may be taken in addition to or in place of the blocks 418, 420. FIGS. 11A, 11B and 11C illustrate three alternative methods of processing the images received at block 416 to provide the basis for the product recommendation steps that follow in the method 400 of FIG. 10. The methods of FIGS. 11A and 11B differ in regard to whether the image is initially analyzed in separate channels or a single channel. The methods of FIGS. 11A and 11B differ in regard to the method of FIG. 11C in the method (automated vs. manual) of locating one or more of the regions of interest in the image.

Although the alternative methods are described with reference to the flowcharts illustrated in FIGS. 11A, B, C, it will be recognized that many other ways for carrying out the methods may exist. For example, the order of the steps may be varied, and steps may be treated as optional or omitted altogether. As one example, both background and color correction need not be carried out by every embodiment. Also, at least part of the method may be embodied in a software program which is stored and executed at the remote site 142. However, certain of the steps of the methods may be performed at or by other devices associated with the network 140, the apparatus 100 for example.

FIG. 11A illustrates a method 500 wherein the image received at block 416 of the method 400 is processed using separate channels. According to one embodiment, three channels may be used for analysis, and may correspond to the R, G, B channels. It will be recognized that the analysis may be undertaken in other color spaces as well.

The method 500 may begin at a block 502, wherein the image is initially processed for the analysis steps to follow. A variety of pre-processing activities may occur at block 502, including filtering of the image, for example. Because the analysis method 500 relies upon analysis in separate channels of a color space, the image is filtered separately in each of the channels. Filtering may occur using a Median or Gaussian filter, for example.

The method 500 may then continue at a block 504, wherein the image is analyzed in separate channels, for example, in each of the R, G, B channels. According to such an embodiment, the tool 200 may have a boundary marker 204 includes at least two regions, those regions having different characteristics in two channels, for example the R and G channels. In each of the channels, an edge detection technique is used to locate the special outlines contained in the image by virtue of the use of the tool 200 in the generation of the image. For example, Canny or Roberts edge detection techniques may be use. Once the edge detection has been carried out in each of the channels, the results are combined to provide a location in the image for each of the special outlines.

Having located the outlines in block 504, the method 500 continues on at block 506. At block 506, knowledge of the shape of the tool 200 is combined with the location of the special outlines to locate various features on the image of the tool 200 and target substrate. For example, the regions of the image corresponding to the boundary marker 206, the color correction scale 208 and the target substrate located in the aperture 204 may be located. The region of the image corresponding to the boundary marker 206 may be referred to as the boundary region, the region of the image corresponding to the color tone scale may be referred to as the color correction scale region, and the region of the image corresponding to the target substrate located in the aperture may be referred to as the target substrate region. Further, regions within each of these regions may be located. For example, color correction regions may be identified within the color correction scale region corresponding to each of the color correction regions of the color correction scale 208.

The method 500 then continues on to blocks 508 and 510, wherein the image is analyzed and corrected for background illumination. While analysis and correction are illustrated as separate steps of the method 500, it will be recognized that the steps may be acted upon as a single action without definable separation. At block 508, the boundary region of the image is analyzed to determine an image gradient. The image gradient is, in turn, used to determine a background correction for the image, which background correction may be used to modify the image to correct for the background illumination conditions occurring at the time the image is generated so as to attempt to bring the actual colors of the image into better congruence with the colors of the tool and target substrate. The image may then be corrected using the background correction at block 510.

The method 500 next analyzes the color correction scale region and applies a color correction at blocks 512, 514. As stated above, while the analysis and correction are illustrated as separate steps, it will be recognized that the steps may be acted upon as a single action without definable separation. Further, the activities undertaken at block 512 may be divided and illustrated separately, even though it was chosen not to so illustrate them in FIG. 10A. In analyzing the color correction scale region, the values for the color correction regions are extracted from the image. These values may then be compared with values stored in a database corresponding to the expected values for such subregions. As noted above, the tool 200 may include an identifier, and the identified may be read from the image to determine which values to retrieve from the database for comparison. Based on the observed values and the expected values, a color correction may be determined. The image may then be corrected according to the color correction at block 514.

With the image now corrected for background illumination and color variation, the method 500 may proceed with the extraction of a set of target substrate region values from the target substrate region of the image at block 516. This activity may be combined with a conversion of the values from the color space in which they were extracted to another color space in which they will be analyzed for the purpose of making the product recommendations. It will be recognized that conversion may also occur prior to extraction; for that matter, conversion may occur as to the entire image before any of the steps of the method 500. With the set of values extracted, the method 500 may pass back to the method 400.

An alternative method 550 is illustrated in FIG. 11B. The method 550 is similar to the method 500, as may be observed from comparison of the flowcharts. That is, blocks 508-516 correspond to blocks 558-566. The method 550 is different than the method 500 in regard to blocks 552, 554. However, the difference is principally one of processing with or without regard for channel separation. In the method 500, blocks 552, 554 are carried out for each channel of a color space, whereas the method 550 does not analyze in separate channels.

A still further alternative method 600 is illustrated in FIG. 11C. This method is similar to the methods 500, 550, as may also be observed from comparison of the flowcharts. That is, blocks 608-616 correspond to blocks 508-516, 558-566. The method 600 is different than the methods 500, 550 in regard to the processing of the image, and in particular in regard to the determination of the location of the target substrate region of the image. According to the method 600, rather than automatically locating the target substrate region using analysis of the image, and in particular the boundary marker region, a manual step occurs before the image is sent for further processing. In the manual step, a person views the image and generates location identification data that represents the location of the target substrate region within the image. The person involved in generating the data may be party identified with the target substrate. Alternatively, the image may be sent to a third-party, who is involved in generating the data regarding region location prior to forwarding the image along for color and/or background correction. The data may be generated through the use of a software tool, for example a drawing tool that permits the person to draw a box or ring about the portion of the image that represents the target substrate region of the image. Once this manual step is completed, then the image and the location identification data are sent for further processing. As such, the method 600 then begins with step 606, wherein this location identification data is received, and after which the method 600 proceeds through steps 608-616 using this location identification data in place of the location determined in association with analysis of a boundary marker region.

It will be recognized that while the boundary marker region is not utilized in the method 600 illustrated in FIG. 11C to determine the target substrate region, a boundary marker region may still be included to permit a background correction to be determined, which correction is used to correct the image for lighting conditions (blocks 608, 610). Alternatively, if the boundary marker region is omitted entirely, the background correction may be determined using other methods.

Returning to the method 400 illustrated in FIG. 10, the customer may be given certain choices and/or informed of certain personal care product recommendations based on the set of values for the tar et substrate region of the image. In one example of use of the apparatus 100, the retail customer may need to make a color choice decision. For example, if the apparatus 100 is being used in conjunction with a hair color product recommendation system, and the customer's hair color analysis results in a bimodal distribution (i.e., primarily two colors are present), the apparatus 100 may ask the customer to choose one of the two colors as the preferred color. Accordingly, the apparatus 100 may display the two choices on an output device 114 (block 422) and receive a selection from the customer (block 424). For example, the apparatus 100 may display two polygon areas of color on a touch sensitive display 114 which may be touched to indicate a selection.

The block 422 may also be used to display comments regarding the state of the image processing occurring at block 418. For example, the method 400 may include displaying options at block 422 in the form of the option to proceed with the remaining steps of the method using the processing as completed, or to start the image capture process over again. For example, it may be that the image processing at 418 produces a set of extracted values that is less than optimal for use in making a product recommendation. Use of the set may not inhibit a recommendation from being made, but it may be preferred to permit the user to choose to proceed or to return to block 406 and being the process over from that point forward, as illustrated by the dashed line in FIG. 10. Of course, such an option may be presented as a mandatory step instead if the set fails to satisfy a statistical analysis of the set, for example. Alternatively, the option may involve returning to some other block of the method 400.

Depending on the various inputs received from the apparatus 100 (personal preference, personal identification, light intensity matrix, option selection), the remote site 142 will generate one or more product and/or service recommendations at block 426. The recommendations may be based on one or more algorithms that compare the set of extracted values and a database of products. Such an algorithm may compare the set of extracted values to a database of colors associated with each of these products. These recommendations are then transferred from the remote site 142 to the apparatus 100 at block 428. The recommended products and/or services may then be displayed to the retail customer via one of the output devices 114 at block 430. For example, the apparatus may display a product name and/or a color.

While the above system, tool and method have been described relative to a target substrate, e.g., skin, hair, teeth, etc., it will be recognized that the system, tool and method may also be used with target materials, other than target substrates, or used with target materials and target substrates. Target materials may include fabrics, silks, etc. that may be used in clothing, for example. Target materials could include building materials, such as wood, paint and wallpaper. Other uses will be recognized.

In summary, persons of ordinary skill in the art will readily appreciate that methods and apparatus for measuring an electromagnetic radiation response property associated with a substrate have been provided. The foregoing description has been presented for the purposes of illustration and description. It is not intended to be exhaustive or to limit the invention to the example embodiments disclosed. Many modifications and variations are possible in light of the above teachings. It is intended that the scope of the invention not be limited by this detailed description of example embodiments, but rather by the claims appended hereto.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A tool comprising:
   a frame comprising an aperture;
   a boundary marker disposed about the aperture, the boundary marker comprising a first marker region disposed about the aperture and a second marker region disposed about the first marker region, the color of the first marker region being different from the color of the second marker region; and
   a color correction scale disposed proximate to the aperture, the color correction scale having at least a first color correction region and a second color correction region, the color of the first and second color correction regions each having an LCh value of between about L=73.5 C=25.3 h=60.4 and about L=32.5 C=11.6 h=48.3.

2. The tool according to claim 1, further comprising a positioning device comprising a connector to attach the tool to a target substrate.

3. The tool according to claim 2, wherein the positioning device comprises one of a hat, a handle, a pair of eyeglasses, or an adhesive strip.

4. The tool according to claim 1, wherein the first and second color correction regions comprise different skin tones, each of the skin tones matching an actual skin tone at at least one lighting condition.

5. The tool according to claim 4, wherein each of the skin tones match an actual skin tone at two lighting conditions.

6. The tool according to claim 5, wherein each of the skin tones are a full spectral match for an actual skin tone.

7. The tool according to claim 4, wherein the color correction scale comprises a third color correction region, the third color correction region comprising a skin tone different than the skin tone of the first color correction region and the skin tone of the second color correction region.

8. The tool according to claim 7, wherein the color correction scale includes fourth and fifth color correction regions, the fourth and fifth color correction regions comprising a first grey tone and a second grey tone.

9. The tool according to claim 1, wherein the aperture has a closed perimeter.

10. The tool according to claim 9, wherein the first marker region comprises a ring disposed about the aperture.

11. The tool according to claim 10, wherein the second marker region comprises a ring disposed concentrically about the first marker region.

12. The tool according to claim 11, wherein the boundary marker comprises a third marker region disposed about the second marker region, the third marker region having a color different than the color of the first marker region and the color of the second marker region.

13. The tool according to claim 1, further comprising an identifier attached to the frame.

14. The tool according to claim 1, wherein at least two of the aperture, the boundary marker and color correction region are coplanar.

15. The tool according to claim 1, wherein the first color correction region and the second color correction region comprise a square shape.

16. The tool according to claim 1, wherein the color correction regions are silk screened to the frame.

17. The tool according to claim 1, wherein the LCh value is determined using a 10-degree observer or a 2-degree observer.

18. The tool according to claim 1, wherein the LCh value is determined using an illuminant selected from the group consisting of D65, A, F2, F7, F11, and TL84.

* * * * *